(12) United States Patent
Bernardon

(10) Patent No.: US 6,326,510 B1
(45) Date of Patent: Dec. 4, 2001

(54) BI-AROMATIC COMPOUNDS, COMPOSITIONS CONTAINING THEM AND USES

(75) Inventor: Jean-Michel Bernardon, Le Rouret (FR)

(73) Assignee: Centre International de Recherches Dermatologiques, Valbonne (FR)

( * ) Notice: Subject to any disclaimer, the term of this patent is extended or adjusted under 35 U.S.C. 154(b) by 0 days.

(21) Appl. No.: 09/171,098

(22) PCT Filed: Feb. 9, 1998

(86) PCT No.: PCT/FR98/00248

§ 371 Date: Jan. 8, 1999

§ 102(e) Date: Jan. 8, 1999

(87) PCT Pub. No.: WO98/34909

PCT Pub. Date: Aug. 13, 1998

(30) Foreign Application Priority Data

Feb. 10, 1997 (FR) .................................................. 97 01501

(51) Int. Cl.$^7$ .................................................. C07C 69/76
(52) U.S. Cl. .................................. 560/56; 560/9; 560/10; 560/75; 564/162; 564/168; 564/173; 564/174; 514/532; 514/613; 549/483; 549/64; 546/314
(58) Field of Search .................................. 560/56, 9, 10, 560/75; 564/162, 168, 173, 174; 549/64, 483; 546/314; 514/532, 613

(56) References Cited

U.S. PATENT DOCUMENTS 5,128,470 7/1992 Klaus et al. .

FOREIGN PATENT DOCUMENTS

| 0 617 020 | 9/1994 | (EP) . |
| 2 735 371 | 12/1996 | (FR) . |
| 92 06948 | 4/1992 | (WO) . |

OTHER PUBLICATIONS

Chemical Abstracts, vol. 85, No. 1, Jul. 5, 1976, Columbus, Ohio, US: Abstract No. 5395, Harita, Kozaburo et al, "Aromatic carboxylic acid amines", XP002044627.

*Primary Examiner*—Paul J. Killos
(74) *Attorney, Agent, or Firm*—Burns, Doane, Swecker & Mathis, L.L.P.

(57) ABSTRACT

The invention relates to novel biaromatic compounds having general formula I (I)

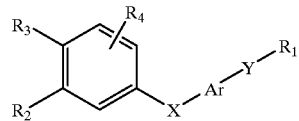

and their use in pharmaceutical compositions for use in human and veterinary medicine, in particular for treating dermatological, rheumatic, respiratory, cardiovascular, and ophthalmological disorders, and for use in cosmetic compositions.

9 Claims, 1 Drawing Sheet

BI-AROMATIC COMPOUNDS, COMPOSITIONS CONTAINING THEM AND USES

FIELD OF THE INVENTION

The invention relates, as novel and useful industrial products, to biaromatic compounds. The invention also relates to the use of these novel compounds in pharmaceutical compositions intended for use in human or veterinary medicine, or alternatively in cosmetic compositions.

BRIEF DESCRIPTION OF THE INVENTION

The compounds according to the invention have pronounced activity in the fields of cell differentiation and proliferation, and find applications more particularly in the topical and systemic treatment of dermatological complaints associated with a keratinization disorder, dermatological (or other) complaints with an inflammatory and/or immunoallergic component, and dermal or epidermal proliferations, whether they are benign or malignant. These compounds can also be used in the treatment of degenerative diseases of connective tissue, to combat ageing of the skin, whether this is light-induced or chronological ageing, and to treat cicatrization disorders. Elsewhere, these compounds find an application in the ophthalmological field, in particular in the treatment of corneopathies.

The compounds according to the invention can also be used in cosmetic compositions for body and hair hygiene.

The compounds according to the invention can be represented by the general formula (I) below:

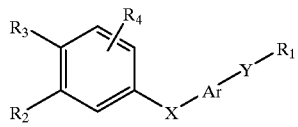

(I)

in which:

| $R_1$ represents | (i) | the radical | —$CH_3$ |
| --- | --- | --- | --- |
| | (ii) | the radical | —$CH_2$—O—$R_5$ |
| | (iii) | the radical | —O—$R_5$ |
| | (iv) | the radical | —CO—$R_6$ |

$R_5$ and $R_6$ having the meanings given below,

Y represents a radical chosen from the radicals of formulae (a) to (c) below:

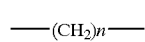

(a)

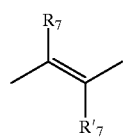

(b)

(c)

$R_7$ and n having the meanings given below,

Ar represents a radical chosen from the radicals of formulae (d) to (g) below:

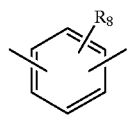

(d)

(e)

(f)

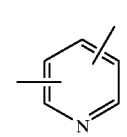

(g)

$R_8$ having the meaning given below,

X represents a radical chosen from the radicals of formulae (h) to (p) below, which can be read from left to right or vice-versa,

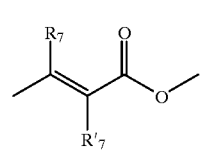

(h)

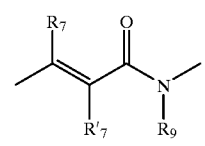

(i)

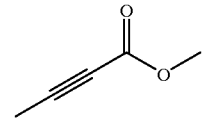

(j)

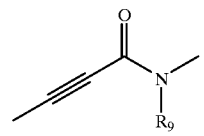

(k)

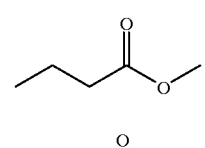

(l)

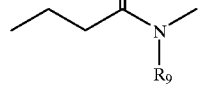

(m)

-continued

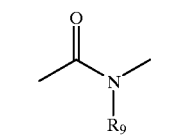

(n)

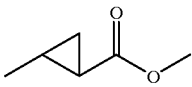

(o)

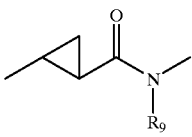

(p)

it being understood that when X represents the radical of formula (n), then Y cannot represent the radical of formula (a), $R_7$ and $R_9$ having the meanings given below, $R_2$ and $R_3$, which may be identical or different, represent an atom or a radical chosen from:

| | |
|---|---|
| (i) | a hydrogen atom, |
| (ii) | a linear or branched alkyl | radical having from 1 to 20 carbon atoms,

| | |
|---|---|
| (iii) | a radical -$OR_5$, |
| (iv) | a radical -$SR_5$, |

$R_5$ having the meaning given below, with the condition that at least one of the radicals $R_2$ and $R_3$ represents a radical having the meaning (ii), it being understood that $R_2$ and $R_3$, taken together, can form, with the adjacent aromatic ring, a 5- or 6-membered ring optionally substituted with methyl groups and/or optionally interrupted by an oxygen or sulphur atom, with the condition that $R_2$ and $R_3$, taken together, form, with the adjacent aromatic ring, a 5- or 6-membered ring optionally substituted with methyl groups and/or optionally interrupted by an oxygen or sulphur atom, when X represents the radical of formula (m) or (i), Y represents the radical of formula (a) with n=0, Ar represents the radical of formula (d), $R_1$ represents the radical —CO—$R_6$ with $R_6$= —O—$R_{11}$ and $R_8$ and $R_9$ represent hydrogen, $R_4$ and $R_8$, which may be identical or different, represent a hydrogen atom, a halogen atom, a linear or branched alkyl radical having from 1 to 20 carbon atoms or a radical —$OR_5$, $R_5$, which may be identical or different, represents a hydrogen atom, a lower alkyl radical or a radical —$COR_{10}$, $R_{10}$ having the meaning given below, $R_6$ represents an atom or a radical chosen from:
(a) a hydrogen atom,
(b) a lower alkyl radical,
(c) a radical of formula:

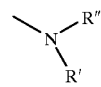

R' and R" having the meanings given below,
(d) a radical —$OR_{11}$ $R_{11}$ having the meaning given below, $R_7$, $R'_7$ and $R_9$, which may be identical or different, represent a hydrogen atom or a lower alkyl radical, n is equal to 0, 1 or 2, $R_{10}$ represents a lower alkyl radical, $R_{11}$ represents a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue.

R' and R", which may be identical or different, represent a hydrogen atom, a lower alkyl radical, a mono- or polyhydroxyalkyl radical, an optionally substituted aryl radical or an amino acid or peptide or sugar residue, or alternatively, taken together, form a heterocycle, and the optical and geometrical isomers of the said compounds of formula (I), as well as the salts thereof.

DETAILED DESCRIPTION OF THE INVENTION

Figure 1:
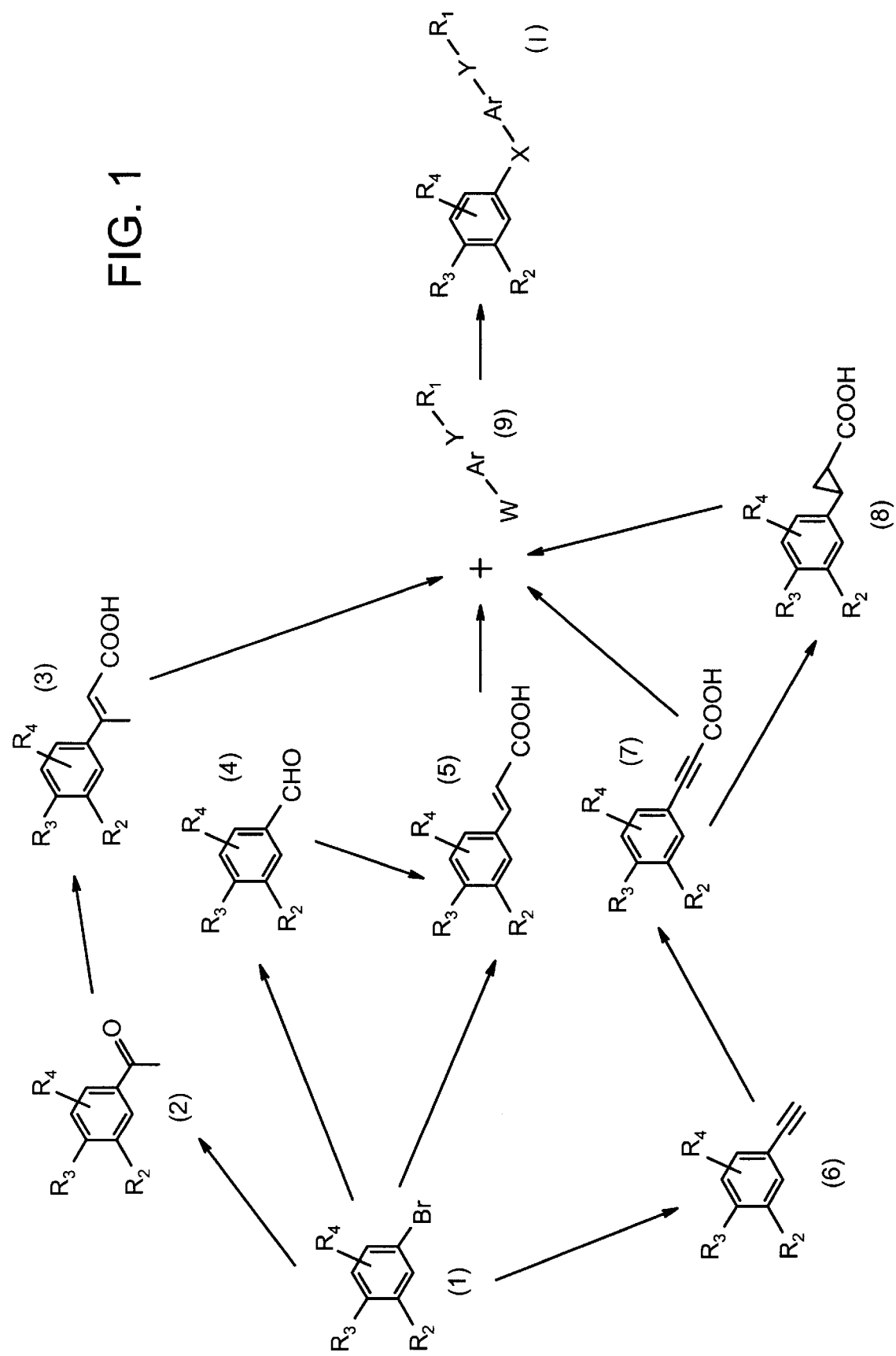
FIG. 1 schematically depicts reaction schemes for synthesis of compounds according to the invention.

When the compounds according to the invention are in the form of salts, by addition of an acid, they are pharmaceutically or cosmetically acceptable salts obtained by addition of an inorganic or organic acid, in particular hydrochloric acid, sulphuric acid, acetic acid, citric acid, fumaric acid, hemisuccinic acid, maleic acid and mandelic acid. When the compounds according to the invention are in the form of salts by addition of a base, they are preferably salts of an alkali metal or alkaline-earth metal or alternatively of zinc or of an organic amine.

According to the present invention, among the linear or branched alkyl radicals having from 1 to 20 carbon atoms, mention may be made advantageously of methyl, ethyl, isopropyl, butyl, tert-butyl, hexyl, octyl, nonyl, 2-ethylhexyl and dodecyl radicals. Preferably, these radicals have from 1 to 12 carbon atoms. When it is lower, the alkyl radical generally comprises from 1 to 10 carbon atoms, preferably from 1 to 6 carbon atoms. Methyl, ethyl, propyl, isopropyl, tert-butyl and hexyl radicals may be mentioned as lower alkyl radical.

Among the linear alkyl radicals having from 1 to 20 carbon atoms, mention may be made, in particular, of methyl, ethyl, propyl, 2-ethylhexyl, octyl, dodecyl, hexadecyl and octadecyl radicals.

Among the branched alkyl radicals having from 1 to 20 carbon atoms, mention may be made in particular of 2-methylbutyl, 2-methylpentyl, 1-methylhexyl, 3-methylheptyl, isopropyl and tert-butyl radicals.

The term alkenyl radical is understood to refer to a radical having from 2 to 20 linear or branched carbon atoms containing one or more double bonds.

Among the alkenyl radicals, a radical containing from 2 to 5 carbon atoms and having one or more ethylenic unsaturations, more particularly such as the allyl radical, is preferred.

The term monohydroxyalkyl or polyhydroxyalkyl radical should be understood to refer to a radical containing from 1 to 6 carbon atoms and from 1 to 5 hydroxyl groups.

Among the monohydroxyalkyl radicals, a radical preferably containing 1 or 3 carbon atoms is preferred, in particular the hydroxymethyl, 2-hydroxyethyl and 2- or 3-hydroxypropyl radicals.

Among the polyhydroxyalkyl radicals, a radical having from 3 to 6 carbon atoms and from 2 to 5 hydroxyl groups is preferred, such as the 2,3-di-hydroxypropyl, 2,3,4-trihydroxybutyl and 2,3,4,5-tetrahydroxypentyl radicals or the pentaerythritol residue.

Among the aryl radicals, a phenyl, thiophene or pyridine radical, optionally substituted with at least one halogen atom, a hydroxyl radical, an alkyl radical, a nitro function, a methoxy group or an optionally substituted amine function, is preferred. The optionally substituted phenyl radical is preferred.

Among the aralkyl radicals, the benzyl or phenethyl radical optionally substituted with at least one halogen atom, a hydroxyl radical, a nitro function or a methoxy group is preferred.

The term sugar residue is understood to refer to a residue derived in particular from glucose, from galactose or from mannose, or alternatively from glucuronic acid.

The term amino acid residue is understood to refer in particular to a residue derived from one of the amino acids such as lysine, glycine or aspartic acid, and the term peptide residue is understood to refer more particularly to a dipeptide or tripeptide residue resulting from the combination of amino acids.

The term heterocycle is preferably understood to refer to a piperidino, morpholino, pyrrolidino or piperazino radical, optionally substituted in position 4 with a $(C_1-C_6)$alkyl or polyhydroxyalkyl radical as defined above.

When the radicals $R_4$ and $R_8$ represent a halogen atom, this is preferably a fluorine, bromine or chlorine atom.

Among the compounds of formula (I) above falling within the context of the present invention, mention may be made of the following:

4-[3-(5,6,7,8-Tetrahydro-5,5,8,8-tetramethyl-2-naphthyl)acryloyloxy]benzoic acid.

4-[3-(5,6,7,8-Tetrahydro-5,5,8,8-tetramethyl-2-naphthyl)acryloylamino]benzoic acid.

4-[3-(5,6,7,8-Tetrahydro-5,5,8,8-tetramethyl-2-naphthyl)propanoyloxy]benzoic acid.

4-[N-Methyl-3-(5,6,7,8-tetrahydro-5,5,8,8-tetramethyl-2-naphthyl)acryloylamino]benzoic acid.

4-[3-(5,6,7,8-Tetrahydro-5,5,8,8-tetramethyl-2-naphthyl)-2-butenoyloxy]benzoic acid.

3-[3-(5,6,7,8-Tetrahydro-5,5,8,8-tetramethyl-2-naphthyl)acryloyloxy]benzoic acid.

4-(5,6,7,8-Tetrahydro-5,5,8,8-tetramethyl-2-naphthyloxycarbonylvinyl)benzoic acid.

4-[3-(5,6,7,8-Tetrahydro-5,5,8,8-tetramethyl-2-naphthyl)propynoyloxy]benzoic acid.

4-[3-(5,6,7,8-Tetrahydro-5,5,8,8-tetramethyl-2-naphthyl)acryloyloxy]benzaldehyde.

4-[3-(5,6,7,8-Tetrahydro-5,5,8,8-tetramethyl-2-naphthyl)acryloyloxy]benzenemethanol.

Methyl 3-{2-[(5,5,8,8-tetramethyl-5,6,7,8-tetrahydro-2-naphthalenecarbonyl)amino]phenyl}acrylate.

Methyl 2-[3-(5,5,8,8-tetramethyl-5,6,7,8-tetrahydro-2-naphthyl)acryloylamino]benzoate.

2-[3-(5,5,8,8-Tetramethyl-5,6,7,8-tetrahydro-2-naphthyl)acryloylamino]benzoic acid.

(E)-2-[3-(5,5,8,8-Tetramethyl-5,6,7,8-tetrahydro-2-naphthyl)but-2-enoylamino]benzoic acid.

Allyl (E)-2-[3-(3,5,5,8,8-pentamethyl-5,6,7,8-tetrahydro-2-naphthyl)acryloyloxy]benzoate.

(E)-2-[3-(3,5,5,8,8-Pentamethyl-5,6,7,8-tetrahydro-2-naphthyl)acryloyloxy]benzoic acid.

Allyl (E)-2-[3-(5,5,8,8-tetramethyl-5,6,7,8-tetrahydro-2-naphthyl)acryloyloxy]benzoate.

Methyl 3-{3-[(5,5,8,8-tetramethyl-5,6,7,8-tetrahydro-2-naphthalenecarbonyl)amino]phenyl}acrylate.

3-{2-[(5,5,8,8-Tetramethyl-5,6,7,8-tetrahydro-2-naphthalenecarbonyl)amino]phenyl}acrylic acid.

2-[3-(5,5,8,8-Tetramethyl-5,6,7,8-tetrahydro-2-naphthyl)acryloyloxy]benzoic acid.

2-[3-(5,5,8,8-Tetramethyl-5,6,7,8-tetrahydro-2-naphthyl)but-2-enoyloxy]benzoic acid.

3-{3-[(5,5,8,8-Tetramethyl-5,6,7,8-tetrahydro-2-naphthalenecarbonyl)amino]phenyl}acrylic acid.

3-{2-[(3,5,5,8,8-Pentamethyl-5,6,7,8-tetrahydro-2-naphthalenecarbonyl)amino]phenyl}acrylic acid.

3-{3-[(3,5,5,8,8-Pentamethyl-5,6,7,8-tetrahydro-2-naphthalenecarbonyl)amino]phenyl}acrylic acid.

4-[2-(5,5,8,8-Tetramethyl-5,6,7,8-tetrahydro-2-naphthyl)cyclopropanecarbonyloxy]benzoic acid.

4-{[2-(5,5,8,8-Tetramethyl-5,6,7,8-tetrahydro-2-naphthyl)cyclopropanecarbonyl]amino}-benzoic acid.

According to the present invention, the compounds of formula (I) which are more particularly preferred are those for which at least one, preferably all, of the conditions below are satisfied:

$R_1$ represents the radical —CO—$R_6$,

Ar represents the radical of formula (d) or (f),

X represents the radical of formula (h), (j), (n) or (o), $R_2$ and $R_3$ have the meaning:

at least one of the two substituents $R_2$ and $R_3$ represents a branched radical having from 1 to 20 carbon atoms, or $R_2$ and $R_3$, taken together, form, with the adjacent aromatic ring, a 5- or 6-membered ring optionally substituted with methyl groups and/or optionally interrupted by an oxygen or sulphur atom.

Even more preferably, the compounds are of formula (I) in which $R_2$ and $R_3$, taken together, form, with the adjacent aromatic ring, a 5- or 6-membered ring optionally substituted with methyl groups and/or optionally interrupted by an oxygen or sulphur atom.

The subject of the present invention is also processes for the preparation of the compounds of formula (I), in particular according to the reaction schemes given in FIG. 1.

The bromo derivatives (1) can be converted:

into aldehyde derivatives (4) by formation of lithium derivatives followed by reaction with DMF;

into ketone derivatives (2) by formation of lithium derivatives followed by reaction with $CO_2$ to form carboxylic acid derivatives and reaction with methyllithium;

into acetylenic derivatives (6) by reaction with trimethylsilylacetylene in the presence of palladium acetate and triphenylphosphine in a solvent such as triethylamine, followed by desilylation in the presence of potassium carbonate or tetrabutylammonium fluoride;

into acrylic acid derivatives (5) by a Heck-type reaction with an acrylic acid ester in the presence of triethylamine or potassium carbonate and palladium acetate and triphenylphosphine, followed by saponification of the ester function with sodium hydroxide or potassium hydroxide in an alcoholic solvent.

The derivatives (3) and (5) can be obtained from the derivatives (2) and (4) respectively by a Horner-Emmons type reaction with triethyl phosphonoacetate in the presence of a base such as sodium hydride, followed by saponification of the ester function with sodium hydroxide or potassium hydroxide in an alcoholic solvent.

The derivatives (7) can be obtained from acetylenic derivatives (6) by lithiation, followed by reaction with $CO_2$.

The cyclopropanecarboxylic derivatives (8) can be obtained by a sequence of reactions starting with the derivatives (7): esterification of the acid function, followed by reaction with diazomethane in the presence of palladium acetate (J. Vallgarda J. Med. Chem. 1996, 39, 1485–1493 and U. Appelberg Bioorg.& Med. Chem. Letters 1996, Vol. 6, No. 4) and saponification in the presence of sodium hydroxide or potassium hydroxide. They can also be obtained by a sequence of reactions comprising reduction of the acid function to an alcohol, followed by protection of this function with, for example, tetrahydropyran, then reaction with chloroform in the presence of sodium hydroxide, deprotection of the alcohol function and oxidation, for example with Jones' reagent (Y. Tanabe Synthesis 1996, 388–92).

The compounds of formula (I) can thus be obtained from the derivatives (3), (5), (7) and (8) by reaction with compounds (9) in which W can represent an amino or hydroxyl radical, either via the acid chloride or in the presence of dicyclohexylcarbodiimide and dimethylaminopyridine in a solvent, such as THF or dichloromethane.

When $R_1$ represents a —COOH radical, the compounds are preferably prepared by protecting $R_1$ with a protecting group of allylic, benzyl or tert-butyl type.

Passage to the free form can be carried out:

in the case of an allylic protecting group, using a catalyst such as certain transition metal complexes in the presence of a secondary amine;

in the case of a benzyl protecting group, by debenzylation in the presence of hydrogen, using a catalyst such as palladium on charcoal;

in the case of a tert-butyl protecting group, using trimethylsilyl iodide.

When $R_1$ represents an alcohol function, the compounds can be obtained from corresponding aldehyde derivatives, by the action of an alkaline hydride, such as sodium borohydride, in an alcoholic solvent (for example methanol).

When $R_1$ represents an amide function, the compounds can be obtained from corresponding carboxylic derivatives by reaction with aliphatic, aromatic or heterocyclic amines, either via an acid chloride or in the presence of dicyclohexylcarbodiimide or carbonyldiimidazole.

The products of general formula (I) thus obtained can be used as starting materials for the manufacture of other compounds of formula (I) according to the invention. These compounds are obtained according to the standard synthetic methods used in chemistry, such as those described in "Advanced Organic Chemistry" by J. March; John Willey and Sons, 1985.

For example, functional modifications of the group $R_1$ can be carried out as indicated below:

| | |
|---|---|
| carboxylic acid -> | ester |
| ester -> | carboxylic acid |
| acid -> | acid chloride |
| acid chloride -> | amide |
| acid -> | amide |
| acid -> | alcohol |
| alcohol -> | aldehyde |
| amide -> | amine |

The compounds according to the invention show activity in the test of differentiation of mouse embryonic teratocarcinoma cells (F9) (Cancer Research 43, p. 5268, 1983) and/or in the test of inhibition of ornithine decarboxylase after induction with TPA in mice (Cancer Research 38, pp. 793–801, 1978). These tests show the activities of these compounds in the fields of cell differentiation and proliferation respectively. In the cell (F9) differentiation test, it is possible to evaluate an agonist activity as an antagonist activity to retinoic acid receptors. The reason for this is that an antagonist is inactive when it is alone in this test, but partially or totally inhibits the effect produced by an agonist retinoid on the morphology and secretion of the plasminogen activator. Some of these compounds are thus also active in a test which consists in identifying RAR-antagonist molecules, as described in French patent application No. 95/07302 filed on Jun. 19 1995 by the Applicant. This test comprises the following steps: (i) a sufficient amount of an RAR-agonist molecule is applied topically to an area of the skin of a mammal, (ii) a molecule capable of showing RAR-antagonist activity is administered systemically or topically to this same mammal or to this same area of the mammal's skin, before, during or after step (i), and (iii) the response on the area of the mammal's skin thus treated is evaluated. Thus, the response to a topical application to a mammal's ear of an RAR-agonist molecule, which corresponds to an increase in the thickness of that ear, can be inhibited by the systemic or topical administration of an RAR-antagonist molecule. In addition, some of these compounds can provide synergism to the biological activity of products which bind to nuclear receptors.

The subject of the present invention is also, as medicaments, the compounds of formula (I) as defined above.

The compounds according to the invention are particularly suitable in the following fields of treatment:

1) for treating dermatological complaints associated with a keratinization disorder which has a bearing on differentiation and on proliferation, in particular for treating common acne, comedones, polymorphonuclear leukocytes, acne rosacea, nodulocystic acne, acne conglobata, senile acne and secondary acnes such as solar acne, medication-induced acne or occupational acne, 2) for treating other types of keratinization disorders, in particular ichthyosis, ichthyosiform states, Darrier's disease, palmoplantar keratoderma, leucoplasias and leucoplasiform states, and cutaneous or mucous (buccal) lichen, 3) for treating other dermatological complaints associated with a keratinization disorder having an inflammatory and/or immunoallergic component and, in particular, all forms of psoriasis, whether it is cutaneous, mucous or ungual psoriasis, and even psoriatic rheumatism, or alternatively cutaneous atopy, such as eczema, or respiratory atopy or alternatively gingival hypertrophy; the compounds may also be used in certain inflammatory complaints which do not exhibit a keratinization disorder, 4) for treating all dermal or epidermal proliferations, whether benign or malignant and whether or not they are of viral origin, such as common warts, flat warts and verruciform epidermodysplasia, it being possible for the oral or florid papillomatoses and the proliferations to be induced by ultraviolet radiation, in particular in the case of basocellular and spinocellular epitheliomas, 5) for treating other dermatological disorders such as bullosis and collagen diseases, 6) for treating certain ophthalmological disorders, in particular corneopathies, 7) for repairing or combating both light-induced and chronological ageing of the skin or for reducing actinic keratoses and pigmentations, or any pathology associated with chronological or actinic ageing, 8) for preventing or curing the stigmata of epidermal and/or dermal atrophy induced by local or systemic corticosteroids, or any other form of skin atrophy, 9) for preventing or treating cicatrization disorders or for preventing or repairing vibices, 10) for combating disorders of sebaceous functioning such as the hyperseborrhoea of acne or simple seborrhoea, 11) in the treatment or prevention of cancerous or precancerous states, more particularly promyelocytic leukaemias, 12) in the treatment of inflammatory complaints such as arthritis, 13) in the treatment of any complaint of viral origin on the skin or generally, such as Kaposi's syndrome, 14) in the prevention or treatment of alopecia, 15) in the treatment of dermatological or general complaints having an immunological component, 16) in the treatment of complaints of the cardiovascular system such as arteriosclerosis or hypertension, as well as insulin-independent diabetes, 17) in the treatment of skin disorders due to exposure to UV radiation.

In the therapeutic fields mentioned above, the compounds according to the invention may advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers. The term D vitamins or derivatives thereof is understood to refer, for example, to vitamin $D_2$ or $D_3$ derivatives and in particular 1,25-dihydroxy vitamin $D_3$. The term anti-free-radical agent is understood to refer, for example, to α-tocopherol, superoxide dismutate, ubiquinol or certain metal-chelating agents. The term α-hydroxy or α-keto acids or derivatives thereof is understood to refer, for example, to lactic acid, malic acid, citric acid, glycolic acid, mandelic acid, tartaric acid, glyceric acid or ascorbic acid or salts, amides or esters thereof. Lastly, the term ion-channel blockers is understood to refer, for example, to Minoxidil (2,4-diamino-6-piperidinopyrimidine 3-oxide) and derivatives thereof.

The subject of the present invention is also medicinal compositions containing at least one compound of formula (I) as defined above, one of the optical or geometrical isomers thereof or one of the salts thereof.

The subject of the present invention is thus a novel medicinal composition intended in particular for treating the abovementioned complaints, and which is characterized in that it comprises, in a pharmaceutically acceptable support which is compatible with the mode of administration selected for this composition, at least one compound of formula (I), one of the optical or geometric isomers thereof or one of the salts thereof.

The compounds according to the invention may be administered enterally, parenterally, topically or ocularly.

Via the enteral route, the medicinal products may be in the form of tablets, gelatin capsules, sugar-coated tablets, syrups, suspensions, solutions, powders, granules, emulsions, microspheres or nanospheres or polymeric or lipid vesicles which allow controlled release. Via the parenteral route, the compositions may be in the form of solutions or suspensions for infusion or for injection.

The compounds according to the invention are generally administered at a daily dose of about 0.01 mg/kg to 100 mg/kg of body weight, taken in 1 to 3 doses.

Via the topical route, the pharmaceutical compositions based on compounds according to the invention are more particularly intended for treating the skin and mucous membranes and may, in this case, be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which allow controlled release. These topical-route compositions may moreover be either in anhydrous form or in an aqueous form, depending on the clinical indication.

Via the ocular route, they are mainly eyedrops.

These compositions for topical or ocular use contain at least one compound of formula (I) as defined above, or one of the optical or geometric isomers thereof, or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin with a tendency towards acne, for promoting the regrowth of the hair, for combating hair loss, for controlling the greasy appearance of the skin or the hair, in protection against the harmful effects of sunlight or in the treatment of physiologically dry skin, and for preventing and/or combating light-induced or chronological ageing.

In the cosmetic field, the compounds according to the invention may also advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers, all of these different products being as defined above.

The present invention is thus also directed towards a cosmetic composition which is characterized in that it comprises, in a cosmetically acceptable support which is suitable for topical application, at least one compound of formula (I) as defined above, or one of the optical or geometric isomers thereof or one of the salts thereof, it being possible for this cosmetic composition to be, in particular, in the form of a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the composition as a whole.

The medicinal and cosmetic compositions according to the invention may also contain inert additives or even pharmacodynamically or cosmetically active additives or combinations of these additives and, in particular, wetting agents; depigmenting agents such as hydroquinone, azelaic acid, caffeic acid or kojic acid; emollients; moisturizing agents such as glycerol, PEG 400, thiamorpholinone and derivatives thereof, or, alternatively, urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,4-diphenylimidazolidine-2,4-dione); non-steroidal anti-inflammatory agents; carotenoids and, in particular, β-carotene; anti-psoriatic agents such as anthraline and derivatives thereof and, lastly, eicosa-5,8,11,14-tetraynoic acid and eicosa-5,8,11-trynoic acid, the esters and the amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as α-tocopherol, butylhydroxyanisole or butylhydroxytoluene.

Several examples for obtaining active compounds of formula (I) according to the invention, as well as various concrete formulations based on such compounds, will now be given by way of illustration and with no limiting nature.

A. EXAMPLES OF COMPOUNDS

Example 1

4-[3-(5,6,7,8-Tetrahydro-5,5,8,8-tetramethyl-2-naphthyl) acryloyloxy]benzoic acid (a) Ethyl 3-(5,6,7,8-tetrahydro-5,5,8,8-tetramethyl-2-naphthyl)acrylate 1.8 g (60 mmol) of sodium hydride (80% in oil) and 50 ml of DMF are introduced into a three-necked flask under a stream of nitrogen. A solution of 11.9 ml (60 mmol) of triethyl phosphonoacetate in 50 ml of DMF is added dropwise and the mixture is stirred until the evolution of gas has ceased. 10.8 g (50 mmol) of 5,6,7,8-tetrahydro-5,5,8,8-tetramethyl-2-naphthalene-carboxaldehyde in 70 ml of DMF are then added and the mixture is stirred at room temperature for four hours. The reaction medium is poured into water and extracted with ethyl ether and the organic phase is separated out after settling has taken place, dried over magnesium sulphate and evaporated. 14.1 g (98%) of the expected ethyl ester are collected in the form of a yellow oil.

(b) 3-(5,6,7,8-Tetrahydro-5,5,8,8-tetramethyl-2-naphthyl)acrylic acid 14.1 g (49.3 mmol) of the above ethyl ester and 200 ml of 2N sodium hydroxide solution are introduced into a round-bottomed flask. The reaction medium is stirred at room temperature for six hours and then evaporated to dryness. The residue is taken up in water, acidified to pH 1 with hydrochloric acid and extracted with ethyl ether and the organic phase is separated out after settling has taken place, washed with water, dried over magnesium sulphate and evaporated. The residue obtained is purified by chromatography on a column of silica eluted with a mixture of ethyl ether and hexane (35–65). After evaporating the solvents, 9 g (71%) of 3-(5,6,7,8-tetrahydro-5,5,8,8-tetramethyl-2-naphthyl)acrylic acid, with a melting point of 220–1° C., are collected.

(c) 3-(5,6,7,8-Tetrahydro-5,5,8,8-tetramethyl-2-naphthyl)acryloyl chloride

A solution of 2.6 g (10 mmol) of 3-(5,6,7,8-tetrahydro-5,5,8,8-tetramethyl-2-naphthyl)acrylic acid in 50 ml of anhydrous dichloromethane is introduced into a round-bottomed flask, 2 ml (10 mmol) of dicyclohexylamine are added and the mixture is stirred for one hour. 800 μl (10 mmol) of thionyl chloride are then added and the mixture is stirred for one hour. The mixture is evaporated to dryness, the residue is taken up in anhydrous ethyl ether, the dicyclohexylamine salt is filtered off and the filtrate is evaporated. 2.8 g (100%) of the crude acid chloride are collected, which product will be used subsequently without further purification.

(d) tert-Butyl 4-[3-(5,6,7,8-tetrahydro-5,5,8,8-tetramethyl-2-naphthyl)acryloyloxy]benzoate 1.94 g (10 mmol) of tert-butyl 4-hydroxy-benzoate, 50 ml of THF and 1.4 ml (11 mmol) of triethylamine are introduced into a round-bottomed flask. A solution of 2.8 g (10 mmol) of the acid chloride prepared above is added dropwise and the mixture is stirred at room temperature for two hours. The reaction medium is poured into water and extracted with ethyl ether, and the organic phase is separated out after settling has taken place, dried over magnesium sulphate and evaporated. The residue obtained is purified by chromatography on a column of silica eluted with dichloromethane. After evaporation of the solvents, 4 g (92w) of the expected tert-butyl ester, with a melting point of 125–6° C., are collected.

(e) 4-[3-(5,6,7,8-Tetrahydro-5,5,8,8-tetramethyl-2-naphthyl)acryloyloxy]benzoic acid 2.8 g (6.4 mmol) of the above tert-butyl ester and 50 ml of carbon tetrachloride are introduced into a round-bottomed flask under a stream of nitrogen, followed by dropwise addition, while cooling to 0° C., of 920 μl (6.4 mmol) of trimethylsilyl iodide. The reaction medium is allowed to return to room temperature, it is poured into water and extracted with ethyl ether, and the organic phase is separated out after settling has taken place, dried over magnesium sulphate and evaporated. The residue obtained is purified by chromatography on a column of silica eluted with ethyl ether. After evaporating the solvents, 2.3 g (96%) of 4-[3-(5,6,7,8-tetrahydro-5,5,8,8-tetramethyl-2-naphthyl) acryloyloxy]benzoic acid, with a melting point of 200–1° C., are collected.

Example 2

4-[3-(5,6,7,8-Tetrahydro-5,5,8,8-tetramethyl-2-naphthyl)acryloylamino]benzoic acid (a) Methyl 4-[3-(5,6,7,8-tetrahydro-5,5,8,8-tetramethyl-2-naphthyl)acryloylamino]benzoate In a similar manner to that of Example 1(d), by reaction of 1.5 g (10 mmol) of methyl 4-amino-benzoate with 2.8 g (10 mmol) of 3-(5,6,7,8-tetrahydro-5,5,8,8-tetramethyl-2-naphthyl)acryloyl chloride, 3.2 g (82%) of the expected methyl ester are obtained.

(b) 4-[3-(5,6,7,8-Tetrahydro-5,5,8,8-tetramethyl-2-naphthyl)acryloylamino]benzoic acid In a similar manner to that of Example 1(b), starting with 3.2 g (8 mmol) of the ethyl ester prepared above, 2.8 g (91%)

of 4-[3-(5,6,7,8-tetrahydro-5,5,8,8-tetramethyl-2-naphthyl) acryloylamino]-benzoic acid, with a melting point of 268–9° C., are obtained.

Example 3

4-[3-(5,6,7,8-Tetrahydro-5,5,8,8-tetramethyl-2-naphthyl)propanoyloxy]benzoic acid (a) Benzyl 4-[3-(5,6,7,8-tetrahydro-5,5,8,8-tetramethyl-2-naphthyl)acryloyloxy]benzoate In a similar manner to that of Example 1 (d), by reaction of 2.3 g (10 mmol) of benzyl 4-hydroxy-benzoate with 2.8 g (10 mmol) of 3-(5,6,7,8-tetrahydro-5,5,8,8-tetramethyl-2-naphthyl)acryloyl chloride, 1.7 g (37%) of the expected benzyl ester, with a melting point 97–9° C., are obtained.

(b) 4-[3-(5,6,7,8-Tetrahydro-5,5,8,8-tetramethyl-2-naphthyl)propanoyloxy]benzoic acid 1.7 g (3.7 mmol) of benzyl 4-[3-(5,6,7,8-tetrahydro-5,5,8,8-tetramethyl-2-naphthyl)acryloyloxy]-benzoate, 40 ml of dioxane and 340 mg of palladium on charcoal (10%) are introduced into a reactor. The mixture is hydrogenated at 40° C. and at a pressure of 7 bar for three hours. The catalyst is filtered off and the mixture is evaporated to dryness. The solid obtained is triturated from hexane, filtered off and dried. 1.2 g (85%) of 4-[3-(5,6,7,8-tetrahydro-5,5,8,8-tetramethyl-2-naphthyl)propanoyloxy]benzoic acid, with a melting point of 183–4° C., are collected.

Example 4

4-[N-Methyl-3-(5,6,7,8-tetrahydro-5,5,8,8-tetramethyl-2-naphthyl) acryloylamino]benzoic acid (a) Methyl 4-[N-methyl-3-(5,6,7,8-tetrahydro-5,5,8,8-tetramethyl-2-naphthyl) acryloylamino]benzoate 300 mg (10 mmol) of sodium hydride (80% in oil) and 30 ml of DMF are introduced into a three-necked flask under a stream of nitrogen. A solution of 1.8 g (4.8 mmol) of methyl 4-[3-(5,6,7,8-tetrahydro-5,5,8,8-tetramethyl-2-naphthyl) acryloylamino]benzoate (prepared in Example 2 (a)) in 50 ml of DMF is added dropwise and the mixture is stirred until the evolution of gas has ceased. 750 μl (12 mmol) of iodomethane are then added and the mixture is stirred at room temperature for four hours. The reaction medium is poured into water and extracted with ethyl ether, and the organic phase is separated out after settling has taken place, dried over magnesium sulphate and evaporated. The solid obtained is triturated from hexane, filtered off and dried. 1.6 g (83%) of the expected methyl ester, with a melting point of 167–8° C., are collected.

(b) 4-[N-Methyl-3-(5,6,7,8-tetrahydro-5,5,8,8-tetramethyl-2-naphthyl) acryloylamino]benzoic acid In a similar manner to that of Example 1(b), starting with 1.6 g (4 mmol) of the methyl ester prepared above, 600 mg (39%) of 4-[N-methyl-3-(5,6,7,8-tetrahydro-5,5,8,8-tetramethyl-2-naphthyl)acryloyl-amino]benzoic acid, with a melting point of 252–3° C., are obtained.

Example 5

4-[3-(5,6, 7,8-Tetrahydro-5,5,8,8-tetramethyl-2-naphthyl)-2-butenoyloxy]benzoic acid (a) Ethyl 3-(5,6,7,8-tetrahydro-5,5,8,8-tetramethyl-2-naphthyl)-2-butenoate In a similar manner to that of Example 1(a), by reaction of 10.9 g (50 mmol) of (5,6,7,8-tetrahydro-5,5,8,8-tetramethyl-2-acetylnaphthalene with 11.9 ml (60 mmol) of triethyl phosphonoacetate, 10.2 g (68%) of the expected ethyl ester are obtained in the form of a colourless oil.

(b) 3-(5,6,7,8-Tetrahydro-5,5,8,8-tetramethyl-2-naphthyl)-2-butenoic acid

In a similar manner to that of Example 1(b), starting with 10.3 g (34 mmol) of the above ethyl ester, 6.1 g (65%) of the expected acid, with a melting point of 173–4° C., are obtained.

(c) 3-(5,6,7,8-Tetrahydro-5,5,8,8-tetramethyl-2-naphthyl)-2-butenoyl chloride

In a similar manner to that of Example 1(c), by reaction of 2.7 g (10 mmol) of 3-(5,6,7,8-tetrahydro-5,5,8,8-tetramethyl-2-naphthyl)-2-butenoic acid with 800 μl of thionyl chloride, 2.9 g (100%) of the expected acid chloride are obtained, which product will be used subsequently in the synthesis without further purification.

(d) tert-Butyl 4-[3-(5,6,7,8-tetrahydro-5,5,8,8-tetramethyl-2-naphthyl)-2-butenoyloxy]benzoate In a similar manner to that of Example 1(d), by reaction of 1.9 g (10 mmol) of tert-butyl 4-hydroxybenzoate with 2.9 g (10 mmol) of the acid chloride prepared above, 3.5 g (80%) of the expected tert-butyl ester are obtained in the form of a yellow oil.

(e) 4-[3-(5,6,7,8-Tetrahydro-5,5,8,8-tetramethyl-2-naphthyl)-2-butenoyloxy]benzoic acid In a similar manner to that of Example 1(e), by reaction of 3.5 g (7.8 mmol) of tert-butyl 4-[3-(5,6,7,8-tetrahydro-5,5,8,8-tetramethyl-2-naphthyl)-2-butenoyloxy]benzoate with 1.1 ml (10 mmol) of trimethylsilyl iodide, 2.3 g (75%) of 4-[3-(5,6,7,8-tetrahydro-5,5,8,8-tetramethyl-2-naphthyl)-2-butenoyloxy]benzoic acid, with a melting point of 170–2° C., are obtained.

Example 6

3-[3-(5,6,7,8-Tetrahydro-5,5,8,8-tetramethyl-2-naphthyl)acryloyloxy]benzoic acid (a) Allyl 3-[3-(5,6,7,8-tetrahydro-5,5,8,8-tetramethyl-2-naphthyl)acryloyloxy]benzoate In a similar manner to that of Example 1(d), by reaction of 2.8 g (10 mmol) of 3-(5,6,7,8-tetrahydro-5,5,8,8-tetramethyl-2-naphthyl)acryloyl chloride with 1.8 g (10 mmol) of allyl 3-hydroxybenzoate, 2.6 g (62%) of the expected allyl ester are obtained in the form of a colourless oil.

(b) 3-[3-(5,6,7,8-Tetrahydro-5,5,8,8-tetramethyl-2-naphthyl)acryloyloxy]benzoic acid 210 mg (6.8 mmol) of sodium hydride (80% in oil) and 15 ml of THF are introduced into a round-bottomed flask under a stream of nitrogen. 1 ml (6.8 mmol) of diethyl malonate is then added dropwise and the mixture is stirred until the evolution of gas has ceased. This solution is introduced dropwise into a mixture of 2.6 g (6.2 mmol) of allyl 3-[3-(5,6,7,8-tetrahydro-5,5,8,8-tetramethyl-2-naphthyl) acryloyloxy]-benzoate, 50 ml of THF and 400 mg of tetrakis-(triphenylphosphine)palladium(0) and the mixture is stirred at room temperature for three hours. The reaction medium is poured into water and extracted with ethyl ether, and the organic phase is separated out after settling has taken place, dried over magnesium sulphate and evaporated. The residue obtained is purified by chromatography on a column of silica eluted with a mixture of ethyl ether and hexane (50/50). After evaporating the solvents, 1.5 g (64%) of 3-[3-(5,6,7,8-tetrahydro-5,5,8,8-tetramethyl-2-naphthyl) acryloyloxy]-benzoic acid, with a melting point of 134–5° C., are collected.

Example 7
4-(5,6,7,8-Tetrahydro-5,5,8,8-tetramethyl-2-naphthyl-oxycarbonylvinyl)benzoic acid (a) Allyl 4-formylbenzoate 3.8 g (12 mmol) of sodium hydride (80% in oil) and 100 ml of DMF are introduced into a three-necked flask under a stream of nitrogen. A solution of 15 g (10 mmol) of 4-formylbenzoic acid in 100 ml of DMF is added dropwise and the mixture is stirred until the evolution of gas has ceased. 10 ml (12 mmol) of allyl bromide are then added and the mixture is stirred at room temperature for four hours. The reaction medium is poured into water and extracted with ethyl ether, and the organic phase is separated out after settling has taken place, dried over magnesium sulphate and evaporated. 17.2 g (90%) of the expected allyl ester are collected in the form of a yellow oil.

(b) 4-Allyloxycarbonyl benzoic acid 17.2 g (90.5 mmol) of allyl 4-formylbenzoate, 24 g (230 mmol) of malonic acid, 8 ml of piperidione and 100 ml of pyridine are introduced into a round-bottomed flask. The reaction medium is heated at 100° C. for six hours and then evaporated to dryness. The residue is taken up in water and dichloromethane and acidified to pH 1, and the organic phase is separated out after settling has taken place, dried over magnesium sulphate and evaporated. The solid obtained is triturated from hexane, filtered off and dried. 16.7 g (80%) of 4-allyloxycarbonylbenzoic acid, with a melting point of 205–6° C., are collected.

(c) 4-Allyloxycarbonylbenzoyl chloride

In a similar manner to that of Example 1(c), starting with 2.3 g (10 mmol) of 4-allyloxycarbonyl-benzoic acid, 2.5 g (100%) of the expected acid chloride are obtained, which product will be used subsequently in the synthesis without further purification.

(d) Allyl 4-(5,6,7,8-tetrahydro-5,5,8,8-tetramethyl-2-naphthyloxycarbonylvinyl) benzoate In a similar manner to that of Example 1(d), by reaction of 2.5 g (10 mmol) of 4-allyloxycarbonylbenzoyl chloride with 2 g (10 mmol) of 5,6,7,8-tetrahydro-5,5,8,8-tetramethyl-2-naphthol, 3.2 g (78%) of the expected allyl ester, with a melting point of 114–5° C., are obtained.

(e) 4-(5,6,7,8-Tetrahydro-5,5,8,8-tetramethyl-2-naphthyloxycarbonylvinyl)benzoic acid In a similar manner to that of Example 6(b), starting with 3.2 g (7.6 mmol) of the above allyl ester, 1.8 g (62w) of 4-(5,6,7,8-tetrahydro-5,5,8,8-tetramethyl-2-naphthyloxycarbonylvinyl)benzoic acid, with a melting point of 226–7° C., are obtained.

Example 8
4-[3-(5,6,7,8-Tetrahydro-5,5,8,8-tetramethyl-2-naphthyl)propynoyloxy]benzoic acid (a) 5,6,7,8-Tetrahydro-5,5,8,8-tetramethyl-2-trimethyl-silylethynylnaphthalene 26.7 g (0.1 mol) of 2-bromo-5,6,7,8-tetrahydro-5,5,8,8-tetramethylnaphthalene, 200 ml of triethylamine and a mixture of 200 mg of palladium acetate and 400 mg of triphenylphosphine are introduced into a three-necked flask under a stream of nitrogen. 20 g (0.204 mol) of trimethylsilylacetylene are then added, the mixture is heated gradually to 90° C. over 1 hour and is left at this temperature for 5 hours. The reaction medium is cooled, the salt is filtered off and the filtrate is evaporated. The residue is taken up in 200 ml of hydrochloric acid (5%) and 400 ml of ethyl ether. The ether phase is separated out after settling has taken place, washed with water, dried over magnesium sulphate and evaporated. The residue obtained is purified by chromatography on a column of silica eluted with hexane. After evaporating the solvents, 18.8 g (66%) of the expected product are collected in the form of a colourless oil.

(b) 5,6,7,8-Tetrahydro-5,5,8,8-tetramethyl-6-ethynyl-naphthalene 5.7 g (0.02 mol) of the above product and 75 ml of methanol are introduced into a round-bottomed flask and 100 mg of potassium carbonate are added. The mixture is stirred at room temperature for 3 hours and then evaporated to dryness, the residue is taken up in water and ethyl ether and the organic phase is separated out after settling has taken place, dried over magnesium sulphate and evaporated. 4.1 g (100%) of the expected acetylene derivative are collected in the form of a yellow oil.

(c) 3-(5,6,7,8-Tetrahydro-5,5,8,8-tetramethyl-2-naphthyl)propargylic acid.

A solution of 4.1 g (19 mmol) of 5,6,7,8-tetrahydro-5,5,8,8-tetramethyl-6-ethynylnaphthalene in 75 ml of THF is introduced into a three-necked flask under a stream of nitrogen, 13.3 ml (21 mmol) of n-butyllithium (2.5M) are added dropwise at −78° C. and the mixture is allowed to return to room temperature. At −78° C., a stream of $CO_2$ is introduced for 30 min and the mixture is allowed to return to room temperature. The reaction medium is poured into saturated ammonium chloride solution and extracted with ethyl ether, and the organic phase is separated out after settling has taken place, dried over magnesium sulphate and evaporated. The residue obtained is triturated with hexane, filtered off and dried. 3.5 g (73%) of the expected propargylic acid, with a melting point of 175–7° C., are collected.

(d) 3-(5,6,7,8-Tetrahydro-5,5,8,8-tetramethyl-2-naphthyl)propynoyl chloride

In a similar manner to that of Example 1(c), starting with 1.28 g (5 mmol) of the above acid, 1.4 g (100%) of the expected acid chloride are obtained, which product will be used subsequently in the synthesis without further purification.

(e) tert-Butyl 4-[3-(5,6,7,8-tetrahydro-5,5,8,8-tetramethyl-2-naphthyl)propynoyloxy]benzoate In a similar manner to that of Example 1(d), by reaction of 1.4 g (5 mmol) of 3-(5,6,7,8-tetrahydro-5,5,8,8-tetramethyl-2-naphthyl)propynoyl chloride with 950 mg (4.9 mmol) of tert-butyl 4-hydroxybenzoate, 1.75 g (83%) of the expected tert-butyl ester are obtained in the form of a yellow oil.

(f) 4-[3-(5,6,7,8-Tetrahydro-5,5,8,8-tetramethyl-2-naphthyl)propynoyloxy]benzoic acid In a similar manner to that of Example 1(e), by reaction of 1.7 g (4 mmol) of tert-butyl 4-[3-(5,6,7,8-tetrahydro-5,5, 8,8-tetramethyl-2-naphthyl)propynoyloxy]benzoate with 580 µl (4 mmol) of trimethylsilyl iodide, 510 mg (34%) of 4-[3-(5,6,7,8-tetrahydro-5,5,8,8-tetramethyl-2-naphthyl) propynoyloxy]benzoic acid, with a melting point of 200–1° C., are obtained.

Example 9

4-[3-(5,6,7,8-Tetrahydro-5,5,8,8-tetramethyl-2-naphthyl)acryloyloxy]benzaldehyde In a similar manner to that of Example 1(d), by reaction of 2.5 g (20 mmol) of 4-hydroxybenzaldehyde with 5.5 g (20 mmol) of 3-(5,6,7,8-tetrahydro-5,5,8,8-tetramethyl-2-naphthyl)acryloyl chloride, 5.6 g (75%) of 4-[3-(5,6,7,8-Tetrahydro-5,5,8,8-tetramethyl-2-naphthyl)acryloyloxy] benzaldehyde, with a melting point of 109–10° C., are obtained.

Example 10

4-[3-(5,6,7,8-Tetrahydro-5,5,8,8-tetramethyl-2-naphthyl)acryloyloxy]benzenemethanol 3.1 g (8.5 mmol) of 4-[3-(5,6,7,8-tetrahydro-5,5,8,8-tetramethyl-2-naphthyl)acryloyloxy]benzaldehyde and 50 ml of a mixture of THF and methanol (50/50) are introduced into a round-bottomed flask. 163 mg (4.25 mmol) of sodium borohydride is added portionwise and the mixture is stirred at [lacuna] temperature for three hours. The reaction medium is poured into water and extracted with ethyl ether, and the organic phase is separated out after settling has taken place, dried over magnesium sulphate, filtered and evaporated. The solid obtained is recrystallized from a mixture of diisopropyl ether and hexane. After filtration and drying, 1.6 g (53%) of 4-[3-(5,6,7,8-tetrahydro-5,5,8,8-tetramethyl-2-naphthyl)acryloyloxy]benzenemethanol, with a melting point of 140–50° C., are collected.

Example 11

Methyl 3-{2-[(5,5,8,8-tetramethyl-5,6,7,8-tetrahydro-2-naphthalenecarbonyl)amino] phenyl}acrylate (a) Methyl 2-aminophenyl acrylate 5 g (22.8 mmol) of 2-iodoaniline, 2 ml (22.8 mmol) of methyl acrylate and 50 ml of triethylamine are introduced into a three-necked flask under a stream of nitrogen. 1.28 g (1.82 mmol) of bis(triphenylphosphine)palladium(II) chloride and 521 mg (2.7 mmol) of CuI are successively added and the mixture is heated at 65° C. for 24 hours. The reaction medium is poured into water and extracted with ethyl acetate, and the organic phase is separated out after settling has taken place, washed with water, dried over magnesium sulphate and evaporated. The residue obtained is purified by chromatography on a column of silica eluted with a mixture of dichloromethane and methanol (95/5). After evaporating the solvents, 3 g (75%) of the expected methyl ester are collected.

(b) Methyl 3-{2-[(5,5,8,8-Tetramethyl-5,6,7,8-tetrahydro-2-naphthalenecarbonyl)amino] phenyl}acrylate 1.13 g (6.38 mmol) of methyl 2-aminophenyl acrylate, 30 ml of THF and 1 ml (7 mmol) of triethylamine are introduced into a round-bottomed flask. A solution of 1.6 g (6.38 mmol) of 5,5,8,8-tetramethyl-5,6,7,8-tetrahydro-2-naphthoyl chloride is added dropwise and the mixture is stirred at room temperature for three hours. The reaction medium is poured into water and extracted with ethyl acetate, and the organic phase is separated out after settling has taken place, washed with water, dried over magnesium sulphate and evaporated. The residue obtained is purified by chromatography on a column of silica eluted with a mixture of heptane and ethyl acetate (95/5). After evaporating the solvents, 2.3 g (92%) of methyl 3-{2-[(5,5,8,8-tetramethyl-5,6,7,8-tetrahydro-2-naphthalenecarbonyl)amino] phenyl}acrylate, with a melting point of 95–6° C., are collected.

Example 12

Methyl 2-[3-(5,5,8,8-tetramethyl-5,6,7,8-tetrahydro2-naphthyl)acryloylamino]benzoate (a) Ethyl 3-(5,6,7,8-tetrahydro-5,5,8,8-tetramethyl-2-naphthyl)acrylate 1.8 g (60 mmol) of sodium hydride (80% in oil) and 50 ml of DMF are introduced into a three-necked flask under a stream of nitrogen. A solution of 11.9 ml (60 mmol) of triethyl phosphonoacetate in 50 ml of DMF is added dropwise and the mixture is stirred until the evolution of gas has ceased. 10.8 g (50 mmol) of 5,6,7,8-tetrahydro-5,5,8,8-tetramethyl-2-naphthalene carboxaldehyde in 70 ml of DMF are then added and the mixture is stirred at room temperature for four hours. The reaction medium is poured into water and extracted with ethyl ether, and the organic phase is separated out after settling has taken place, dried over magnesium sulphate and evaporated. 14.1 g (98%) of the expected ethyl ester are collected in the form of a yellow oil.

(b) 3-(5,6,7,8-Tetrahydro-5,5,8,8-tetramethyl-2-naphthyl)acrylic acid 14.1 g (49.3 mmol) of the above ethyl ester and 200 ml of 2N sodium hydroxide solution are introduced into a round-bottomed flask. The reaction medium is stirred at room temperature for six hours and is then evaporated to dryness. The residue is taken up in water, acidified to pH 1 with hydrochloric acid and extracted with ethyl ether, and the organic phase is separated out after settling has taken place, washed with water, dried over magnesium sulphate and evaporated. The residue obtained is purified by chromatography on a column of silica eluted with a mixture of ethyl ether and hexane (35/65). After evaporating the solvents, 9 g (71%) of 3-(5,6,7,8-tetrahydro-5,5,8,8-tetramethyl-2-naphthyl)acrylic acid, with a melting point of 220–1° C., are collected.

(c) 3-(5,6,7,8-Tetrahydro-5,5,8,8-tetramethyl-2-naphthyl)acryloyl chloride

A solution of 2.6 g (10 mmol) of 3-(5,6,7,8-tetrahydro-5,5,8,8-tetramethyl-2-naphthyl)acrylic acid in 50 ml of anhydrous dichloromethane is introduced into a round-bottomed flask, 2 ml (10 mmol) of dicyclohexylamine are added and the mixture is stirred for one hour. 800 µl (10 mmol) of thionyl chloride are then added and the mixture is stirred for one hour. The mixture is evaporated to dryness, the residue is taken up in anhydrous ethyl ether, the dicyclohexylamine salt is filtered off and the filtrate is evaporated. 2.8 g (100%) of the crude acid chloride are collected, which product will be used subsequently in the synthesis without further purification.

(d) Methyl 2-[3-(5,5,8,8-tetramethyl-5,6,7,8-tetrahydro-2-naphthyl)acryloylamino]benzoate 1.18 g (7.8 mmol) of methyl 2-aminobenzoate and 10 ml of THF are introduced into a round-bottomed flask. A solution of 1.08 g (3.9 mmol) of the acid chloride prepared above in 10 ml of THF is added dropwise and the mixture is stirred at room temperature for two hours. The reaction medium is poured into water and extracted with ethyl ether, and the organic phase is separated out after settling has taken place, dried over magnesium sulphate and evaporated. The residue obtained is purified by chromatography on a column of silica eluted with ethyl acetate. After evaporating the solvents, 750 mg (49%) of methyl 2-[3-(5,5,8,8-tetramethyl-5,6,7,8-tetrahydro-2-naphthyl)acryloylamino]-benzoate, with a melting point of 132–3° C., are collected.

Example 13

2-[3-(5,5,8,8-Tetramethyl-5,6,7,8-tetrahydro-2-naphthyl)acryloylamino]benzoic acid 540 mg (1.38 mmol) of methyl 2-[3-(5,5,8,8-tetramethyl-5,6,7,8-tetrahydro-2-naphthyl)acryloylamino]benzoate, 5 ml of THF and 5 ml of methanol are introduced into a round-bottomed flask. 5.5 ml of methanolic sodium hydroxide solution (2N) are added and the mixture is stirred at room temperature for four hours. The reaction medium is poured into water, acidified to pH 1 with hydrochloric acid and extracted with ethyl acetate, and the organic phase is separated out after settling has taken place, washed with water, dried over magnesium sulphate and evaporated. The residue obtained is purified by chromatography on a column of silica eluted with a mixture of heptane and ethyl acetate (95/5). After evaporating the solvents, 400 mg (77%) of the expected acid, with a melting point of 185–6° C., are collected.

Example 14

(E)-2-[3-(5,5,8,8-Tetramethyl-5,6,7,8-tetrahydro-2-naphthyl )but-2-enoylamino]benzoic acid (a) Ethyl 3-(5,6,7,8-tetrahydro-5,5,8,8-tetramethyl-2-naphthyl)-2-butenoate In a similar manner to that of Example 1(a), by reaction of 10.9 g (50 mmol) of (5,6,7,8-tetrahydro-5,5,8,8-tetramethyl-2-acetylnaphthalene with 11.9 ml (60 mmol) of triethyl phosphonoacetate, 10.2 g (68%) of the expected ethyl ester are obtained in the form of a colourless oil.

(b) 3-(5,6,7,8-Tetrahydro-5,5,8,8-tetramethyl-2-naphthyl)-2-butenoic acid

In a similar manner to that of Example 1(b), starting with 10.3 g (34 mmol) of the above ethyl ester, 6.1 g (65%) of the expected acid, with a melting pint of 173–4° C., are obtained.

(c) 3-(5,6,7,8-Tetrahydro-5,5,8,8-tetramethyl-2-naphthyl)-2-butenoyl chloride

In a similar manner to that of Example 1(c), by reaction of 2.7 g (10 mmol) of 3-(5,6,7,8-tetrahydro-5,5,8,8-tetramethyl-2-naphthyl)-2-butenoic acid with 800 μl of thionyl chloride, 2.9 g (100%) of the expected acid chloride are obtained, which product will be used subsequently in the synthesis without further purification.

(d) Methyl (E)-2-[3-(5,5,8,8-tetramethyl-5,6,7,8-tetrahydro-2-naphthyl)but-2-enoylamino]benzoate In a similar manner to that of Example 11(b), by reaction of 400 μl (3.1 mmol) of methyl 2-aminobenzoate with 900 mg (3.1 mmol) of the acid chloride prepared above, 350 mg (30%) of the expected methyl ester are obtained in the form of a yellow oil.

(e) (E)-2-[3-(5,5,8,8-Tetramethyl-5,6,7,8-tetrahydro-2-naphthyl)but-2-enoylamino]benzoic acid In a similar manner to that of Example 13, starting with 170 mg (4.2 mmol) of the above methyl ester, 140 mg (85%) of (E)-2-[3-(5,5,8,8-tetramethyl-5,6,7,8-tetrahydro-2-naphthyl)but-2-enoylamino]benzoic acid, with a melting point of 175–6° C., are obtained.

Example 15

Allyl (E)-2-[3-(3,5,5,8,8-pentamethyl1–5,6,7,8-tetrahydro-2-naphthyl)acryloyloxy]benzoate (a) Ethyl 3-(3,5,5,8,8-pentamethyl-5,6,7,8-tetrahydro-2-naphthyl)acrylate In a similar manner to that of Example 12(a), by reaction of 4 g (17.4 mmol) of 3,5,5,8,8-pentamethyl-5,6,7,8-tetrahydro-2-naphthylcarboxaldehyde with 4.15 ml (20.9 mmol) of triethyl phosphonoacetate, 4.91 g (94%) of ethyl 3-(3,5,5,8,8-pentamethyl-5,6,7,8-tetrahydro-2-naphthyl)acrylate are obtained.

(b) 3-(3,5,5,8,8-Pentamethyl-5,6,7,8-tetrahydro-2-naphthyl)acrylic acid

In a similar manner to that of Example 12(b), starting with 4.7 g (15.9 mmol) of the above ethyl ester, 3.66 g (84%) of 3-(3,5,5,8,8-pentamethyl-5,6,7,8-tetrahydro-2-naphthyl) acrylic acid are obtained.

(c) 3-(3,5,5,8,8-Pentamethyl-5,6,7,8-tetrahydro-2-naphthyl)acryloyl chloride

In a similar manner to that of Example 12(c), starting with 2 g (7.3 mmol) of the above acid, 2.2 g (100%) of the acid chloride are obtained, which product is used subsequently in the synthesis without further purification.

(d) Allyl (E)-2-[3-(3,5,5,8,8-pentamethyl-5,6,7,8-tetrahydro-2-naphthyl)acryloyloxy]benzoate In a similar manner to that of Example 11(b), by reaction of 1.15 g (6.44 mmol) of allyl 4-hydroxybenzoate with 1.7 g (5.85 mmol) of 3-(3,5,5,8,8-pentamethyl-5,6,7,8-tetrahydro-2-naphthyl)acryloyl chloride, 1.8 g (71%) of the expected allyl ester, with a melting point of 86–7° C., are obtained.

Example 16

(E)-2-[3-(3,5,5,8,8-Pentamethyl-5.6,7,8-tetrahydro-2-naphthyl) acryloyloxy]benzoic acid 117 mg (4.9 mmol) of sodium hydride (80% in oil) and 15 ml of THF are introduced into a round-bottomed flask under a stream of nitrogen. 540 μl (3.6 mmol) of diethyl malonate are then added dropwise and the mixture is stirred until the evolution of gas has ceased. This solution is introduced dropwise into a mixture of 1.4 g (3.24 mmol) of allyl (E)-2-[3-(3,5,5,8,8-pentamethyl-5,6,7,8-tetrahydro-2-naphthyl)acryloyloxy]benzoate, 20 ml of THF and 187 mg of tetrakis(triphenylphosphine)palladium(0) and stirred at room temperature for three hours. The reaction medium is poured into water and extracted with ethyl ether, and the organic phase is separated out after settling has taken place, dried over magnesium sulphate and evaporated. The residue obtained is purified by chromatography on a column of silica eluted with a mixture of heptane and ethyl acetate (95/5). After evaporating the solvents, 800 mg (63%) of (E)-2-[3-(3,5,5,8,8-pentamethyl-5,6,7,8-tetrahydro-2-naphthyl) acryloyloxy]benzoic acid, with a melting point of 137–8° C., are collected.

Example 17

Allyl (E)-2-[3-(5,5,8,8-tetramethyl-5,6,7,8-tetrahydro-2-naphthyl)acryloyloxy]benzoate In a similar manner to that of Example 11(b), by reaction of 710 mg (4 mmol) of allyl 4-hydroxybenzoate with 1 g (3.62 mmol) of 3-(5,6,7,8-tetrahydro-5,5,8,8-tetramethyl-2-naphthyl)acryloyl chloride obtained in Example 1(c), 500 mg (33%) of allyl E)-2-[3-(5,5,8,8-tetramethyl-5,6,7,8-tetrahydro-2-naphthyl)acryloyloxy]benzoate, with a melting point of 92–3° C., are obtained.

Example 18

Methyl 3-{3-[(5,5,8,8-tetramethyl-5,6,7,8-tetrahydro-2-naphthalenecarbonyl)amino]phenyl] acrylate (a) Methyl 3-aminophenyl acrylate 8 g (36.5 mmol) of 3-iodoaniline, 3.3 ml (36.5 mmol) of methyl acrylate and 50 ml of triethylamine are introduced into a three-necked flask under a stream of nitrogen. The reaction medium is degassed, 410 mg (1.82 mmol) of palladium acetate are added and the mixture is heated at 65° C. for 2 hours. The reaction medium is poured into water and extracted with ethyl acetate, and the organic phase is separated out after settling has taken place, washed with water, dried over magnesium sulphate and evaporated. The residue obtained is purified by chromatography on a column of silica eluted with dichloromethane. After evaporating the solvents, 4 g (62%) of the expected methyl ester are collected.

(b) Methyl 3-{3-[(5,5,8,8-tetramethyl-5,6,7,8-tetrahydro-2-naphthalenecarbonyl)(c)amino]phenyl] acrylate 2.07 g (11.7 mmol) of methyl 3-(3-aminophenyl)acrylate, 30 ml of THF and 1.8 ml (12.9 mmol) of triethylamine are introduced into a round-bottomed flask. A solution of 2.93 g (11.7 mmol) of 5,5,8,8-tetramethyl-5,6,7,8-tetrahydronaphthoyl chloride is added dropwise and the mixture is stirred at room temperature for three hours. The reaction medium is poured into water and extracted with ethyl acetate, and the organic phase is separated out after settling has taken place, washed with water, dried over magnesium sulphate and evaporated. The residue obtained is purified by chromatography on a column of silica eluted with a mixture of heptane and dichloromethane (10/90). After evaporating the solvents, 3.8 g (83%) of methyl 3-{3-[(5,5,8,8-tetramethyl-5,6,7,8-tetrahydro-2-naphthalenecarbonyl)amino]phenyl}acrylate, with a melting point of 212–3° C., are collected.

Example 19

3-{2-[(5,5,8,8-Tetramethyl-5,6,7,8-tetrahydro-2-naphthalenecarbonyl)amino]phenyl}acrylic acid In a similar manner to that of Example 13, starting with 650 mg (1.66 mmol) of methyl 3-{2-[(5,5,8,8-tetramethyl-5,6,7,8-tetrahydro-2-naphthalenecarbonyl)amino] phenyl}acrylate, 350 mg (56w) of 3-{2-[(5,5,8,8-tetramethyl-5,6,7,8-tetrahydro-2-naphthalenecarbonyl) amino]phenyl}acrylic acid, with a melting point of 205–6° C., are obtained.

Example 20

2-[3-(5,5,8,8-Tetramethyl-5,6,7,8-tetrahydro-2-naphthyl)acryloyloxy]benzoic acid In a similar manner to that of Example 16, starting with 400 mg (0.96 mmol) of allyl E)-2-[3-(5,5,8,8-tetramethyl-5,6,7,8-tetrahydro-2-naphthyl)-acryloyloxy]benzoate obtained in Example 17, 200 mg (55%) of 2-[3-(5,5,8,8-tetramethyl-5,6,7,8-tetrahydro-2-naphthyl)acryloyloxy] benzoic acid, with a melting point of 135–6° C., are obtained.

Example 21

2-[3-(5,5,8,8-Tetramethyl-5,6,7,8-tetrahydro-2-naphthyl)but-2-enoyloxy]benzoic acid (a) Allyl 2-[3-(5,5,8,8-tetramethyl-5,6,7,8-tetrahydro-2-naphthyl)but-2-enoyloxy]benzoate In a similar manner to that of Example 11(b), by reaction of 607 mg (3.4 mmol) of allyl 4-hydroxybenzoate with 900 mg (3.1 mmol) of 3-(5,6,7,8-tetrahydro-5,5,8,8-tetramethyl-2-naphthyl)-2-butenoyl chloride prepared in Example 5(c), 420 mg (31%) of the expected allyl ester are obtained.

(b) 2-[3-(5,5,8,8-Tetramethyl-5,6,7,8-tetrahydro-2-naphthyl)but-2-enoyloxy]benzoic acid In a similar manner to that of Example 16, starting with 120 mg (0.28 mmol) of allyl 2-[3-(5,5,8,8-tetramethyl-5,6,7,8-tetrahydro-2-naphthyl)but-2-enoyloxy]benzoate, 70 mg (64%) of 2-[3-(5,5,8,8-tetramethyl-5,6,7,8-tetrahydro-2-naphthyl)but-2-enoyloxy]benzoic acid, with a melting point of 128–9° C., are obtained.

Example 22

3-{3-[(5,5,8,8-Tetramethyl-5,6,7,8-tetrahydro-2-naphthalenecarbonyl)amino]phenyl}acrylic acid 2.9 g (7.4 mmol) of methyl 3-{3-[(5,5,8,8-tetramethyl-5,6,7,8-tetrahydro-2-naphthalenecarbonyl)-amino] phenyl}acrylate obtained in Example 18, 50 ml of THF and 3.1 g (74 mmol) of lithium hydroxide are introduced into a round-bottomed flask. The reaction medium is refluxed for 24 hours and then poured into water, acidified to pH 1 with concentrated hydrochloric acid and extracted with ethyl acetate, and the organic phase is separated out after settling has taken place, washed with water, dried over magnesium sulphate and evaporated. The residue obtained is triturated from heptane, filtered off and dried. 2.8 g (100%) of 3-{3-[(5,5,8,8- tetramethyl-5,6,7,8-tetrahydro-2-naphthalenecarbonyl) amino]phenyl}acrylic acid, with a melting point of 215–6° C., are collected.

Example 23

3-{2-[(3,5,5,8,8-Pentamethyl-5,6,7,8-tetrahydro-2-naphthalenecarbonyl)amino]phenyl}acrylic acid (a) 3,5,5,8,8-Pentamethyl-5,6,7,8-tetrahydro-2-naphthoyl chloride In a similar manner to that of Example 12(c), starting with 3.84 g (15.6 mmol) of 3,5,5,8,8-pentamethyl-5,6,7,8- tetrahydro-2-naphthoic acid, 4.12 g (100%) of acid chloride are obtained, which product is used subsequently in the synthesis without further purification.

(b) Methyl 3-{2-[(3,5,5,8,8-pentamethyl-5,6,7,8-tetrahydro-2-naphthalenecarbonyl)amino]phenyl}acrylate In a similar manner to that of Example 18(b), by reaction of 983 mg (5.6 mmol) of methyl 3-(2-aminophenyl)acrylate with 1.47 g (5.6 mmol) of the above acid chloride, 270 mg (12%) of methyl 3-{2-[(3,5,5,8,8-pentamethyl-5,6,7,8-tetrahydro-2-naphthalenecarbonyl)-amino]phenyl}acrylate are obtained.

(c) 3-{2-[(3,5,5,8,8-Pentamethyl-5,6,7,8-tetrahydro-2-naphthalenecarbonyl)amino]phenyl}acrylic acid In a similar manner to that of Example 13, starting with 240 mg (0.59 mmol) of the above methyl ester, 180 mg (81%) of 3-{2-[(3,5,5,8,8-pentamethyl-5,6,7,8-tetrahydro-2-naphthalenecarbonyl)amino]phenyl}-acrylic acid, with a melting point of 218–9° C., are obtained.

Example 24

3-{3-[ (3,5,5,8,8-Pentamethyl-5,6,7,8-tetrahydro-2-naphthalenecarbonyl)amino]phenyl}acrylic acid (a) Methyl 3-{3-[(3,5,5,8,8-pentamethyl-5,6,7,8-tetrahydro-2-naphthalenecarbonyl)amino]phenyl}acrylate In a similar manner to that of Example 18(b), by reaction of 940 mg (5.3 mmol) of methyl 3-(3-amino-phenyl)acrylate with 1.4 g (5.3 mmol) of 3,5,5,8,8-pentamethyl-5,6,7,8-tetrahydro-2-naphthoyl chloride prepared in Example 23(a), 330 mg (15w) of methyl 3-{3-[(3,5,5,8,8-pentamethyl-5,6,7,8-tetrahydro-2-naphthalenecarbonyl)amino]phenyl}acrylate are obtained.

(b) 3-{3-[(3,5,5,8,8-Pentamethyl-5,6,7,8-tetrahydro-2-naphthalenecarbonyl)amino]phenyl}acrylic acid In a similar manner to that of Example 13, starting with 300 mg (0.74 mmol) of 3-{3-[(3,5,5,8,8-pentamethyl-5,6,7,8-tetrahydro-2-naphthalenecarbonyl)-amino]phenyl}acrylate, 220 mg (79%) of 3-{3-[(3,5,5,8,8-pentamethyl-5,6,7,8-tetrahydro-2-naphthalenecarbonyl)amino]phenyl}acrylic acid, with a melting point of 205–6° C., are obtained.

Example 25

4-[2-(5 5,8,8-Tetramethyl-5,6,7,8-tetrahydro-2-naphthyl)cyclopropanecarbonyloxy]benzoic acid (a) (E)-N-Methoxy-N-methyl-3-(5,5,8,8-tetramethyl-5,6,7,8-tetrahydro-2-naphthyl)acrylamide 727 mg (7.45 mmol) of N,O-dimethylhydroxyl-amine hydrochloride, 10 ml of THF and 2.3 ml (16.4 mmol) of triethylamine are introduced into a three-necked flask under a stream of nitrogen. A solution of 2.06 g (7.45 mmol) of 3-(5,6,7,8-tetrahydro-5,5,8,8-tetramethyl-2-naphthyl)acryloyl chloride prepared in Example 1(c) in 20 ml of THF is added dropwise and the mixture is stirred at room temperature for six hours. The reaction medium is poured into water and extracted with ethyl acetate, and the organic phase is separated out after settling has taken place, dried over magnesium sulphate and evaporated. The residue obtained is purified by chromatography on a column of silica eluted with a mixture of heptane and ethyl acetate (80/20). After evaporating the solvents, 1 g (45%) of (E)-N-methoxy-N-methyl-3-(5,5,8,8-tetramethyl-5,6,7,8-tetrahydro-2-naphthyl)acrylamide is collected in the form of an oil.

(b) N-Methoxy-N-methyl-2-(5,5,8,8-tetramethyl-5,6,7,8-tetrahydro-2-naphthyl)cyclopropanecarboxamide 660 mg (3.3 mmol) of trimethylsulphoxonium iodide and 3 ml of DMSO are introduced into a three-necked flask under a stream of nitrogen. 100 mg (4.12 mmol) of sodium hydride (80% in oil) are added portionwise and the mixture is stirred until the evolution of gas has ceased. A solution of 900 mg (3 mmol) of (E)-N-methoxy-N-methyl-3-(5,5,8,8-tetramethyl-5,6,7,8-tetrahydro-2-naphthyl)acrylamide in 15 ml of DMSO is then added dropwise and the mixture is stirred at room temperature for two hours. The reaction medium is poured into water and extracted with ethyl acetate, and the organic phase is separated out after settling has taken place, dried over magnesium sulphate and evaporated. The residue obtained is purified by chromatography on a column of silica eluted with a mixture of heptane and ethyl acetate (80/20). After evaporating the solvents, 400 mg (43%) of N-methoxy-N-methyl-2-(5,5,8,8-tetramethyl-5,6,7,8-tetrahydro-2-naphthyl)cyclopropanecarboxamide are collected in the form of an oil.

(c) 2-(5,5,8,8-Tetramethyl-5,6,7,8-tetrahydro-2-naphthyl)(d)cyclopropanecarboxylic acid 360 mg (1.14 mmol) of N-methoxy-N-methyl-2-(5,5,8,8-tetramethyl-5,6,7,8-tetrahydro-2-naphthyl)-cyclopropanecarboxamide, 15 ml of ethyl ether, 842 mg (7.5 mmol) of potassium tert-butoxide and 68.4 μl of water are introduced into a round-bottomed flask. The reaction medium is stirred at room temperature for three hours and then poured into water, acidified to pH 3 with hydrochloric acid and extracted with ethyl ether, and the organic phase is separated out after settling has taken place, dried over magnesium sulphate and evaporated. 280 mg (90%) of 2-(5,5,8,8-tetramethyl-5,6,7,8-tetrahydro-2-naphthyl)cyclopropanecarboxylic acid are collected.

(d) 2-(5,5,8,8-Tetramethyl-5,6,7,8-tetrahydro-2-naphthyl)cyclopropanecarboxylic acid chloride.

In a similar manner to that of Example 1(c), starting with 190 mg (0.7 mmol) of 2-(5,5,8,8-tetra-methyl-5,6,7,8-tetrahydro-2-naphthyl)cyclopropane-carboxylic acid, 124 mg (61%) of the expected acid chloride are obtained.

(e) Allyl 4-[2-(5,5,8,8-tetramethyl-5,6,7,8-tetrahydro-2-naphthyl)(f)cyclopropanecarbonyloxy]benzoate In a similar manner to that of Example 18(b), by reaction of 76.2 mg (0.43 mmol) of allyl 4-hydroxybenzoate with 124 mg (0.43 mmol) of the above acid chloride, 120 mg (65%) of allyl 4-[2-(5,5,8,8-tetra-methyl-5,6,7,8-tetrahydro-2-naphthyl)cyclopropane-carbonyloxy]benzoate are obtained.

(f) 4-[2-(5,5,8,8-Tetramethyl-5,6,7,8-tetrahydro-2-naphthyl)cyclopropanecarbonyloxy]benzoic acid In a similar manner to that of Example 16, starting with 110 mg (0.25 mmol) of allyl 4-[2-(5,5,8,8-tetramethyl-5,6, 7,8-tetrahydro-2-naphthyl)cyclopropanecarbonyloxy]benzoate, 75 mg (75%) of 4-[2-(5,5,8,8-tetramethyl-5,6,7,8-tetrahydro-2-naphthyl)cyclopropanecarbonyloxy]benzoic acid, with a melting point of 191–2° C., are obtained.

Example 26

4-{[2-(5,5,8,8-Tetramethyl-5,6,7,8-tetrahydro-2-naphthyl)cyclopropanecarbonyl]amino}benzoic acid (a) Allyl 4-{[2-(5,5,8,8-tetramethyl-5,6,7,8-tetrahydro-2-naphthyl)(b)cyclopropanecarbonyl]-amino}benzoate In a similar manner to that of Example 18(b), by reaction of 96 mg (0.54 mmol) of allyl 4-aminobenzoate with 155 mg (0.54 mmol) of the acid chloride prepared in Example 25(d), 165 mg (71) of allyl 4-{[2-(5,5,8,8-tetramethyl-5,6,7,8-tetrahydro-2-naphthyl)cyclopropanecarbonyl]amino}benzoate are obtained.

(b) 4-{[2-(5,5,8,8-Tetramethyl-5,6,7,8-tetrahydro-2-naphthyl)(c)cyclopropanecarbonyl]amino}benzoic acid In a similar manner to that of Example 16, starting with 200 mg (0.3 mmol) of allyl 4-{[2-(5,5,8,8-tetramethyl-5,6,7,8-tetrahydro-2-naphthyl)cyclopropanecarbonyl]amino}benzoate, 100 mg (85%) of 4-{[2-(5,5,8,8-tetramethyl-5,6,7,8-tetrahydro-2-naphthyl)cyclopropanecarbonyl]amino}benzoic acid, with a melting point of 230–1° C., are obtained.

B. FORMULATION EXAMPLES

1) Oral Route (a) The following composition is prepared in the form of a 0.8 g tablet

| | |
|---|---|
| Compound of Example 1 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets will be administered to an adult individual per day for 3 to 6 months, depending on the severity of the case treated.

(b) A drinkable suspension, intended to be packaged in 5 ml vials, is prepared

| | |
|---|---|
| Compound of Example 2 | 0.050 g |
| Glycerol | 0.500 g |
| 70% sorbitol | 0.500 g |
| Sodium saccharinate | 0.010 g |
| Methyl para-hydroxybenzoate | 0.040 g |
| Flavouring q.s. | |
| Purified water q.s. | 5 ml |

For the treatment of acne, 1 vial will be administered to an adult individual per day for 3 months, depending on the severity of the case treated.

(c) The following formulation intended to be packaged in gelatin capsules is prepared:

| | |
|---|---|
| Compound of Example 3 | 0.025 g |
| Corn starch | 0.060 g |
| Lactose q.s. | 0.300 g |

The gelatin capsules used consist of gelatin, titanium oxide and a preserving agent.

In the treatment of psoriasis, 1 gelatin capsule will be administered to an adult individual per day for 30 days.

2) Topical Route (a) The following nonionic water-in-oil cream is prepared:

| | |
|---|---|
| Compound of Example 6 | 0.100 g |
| Mixture of emulsifying lanolin alcohols, waxes and purified oils, sold by the company BDF under the name "anhydrous eucerin" | 39.900 g |
| Methyl para-hydroxybenzoate | 0.075 g |
| Propyl para-hydroxybenzoate | 0.075 g |
| Sterile demineralized water q.s. | 100.000 g |

This cream will be applied to psoriatic skin 1 to 2 times a day for 30 days.

(b) A gel is prepared by making the following formulation:

| | |
|---|---|
| Compound of Example 8 | 0.050 g |
| Base erythromycin | 4.000 g |
| Butylhydroxytoluene | 0.050 g |
| Hydroxypropylcellulose sold by the company Hercules under the name "Klucel HF" | 2.000 g |
| Ethanol (at 95°) q.s. | 100.000 g |

This gel will be applied to skin affected with dermatitis or acneic skin 1 to 3 times a day for 6 to 12 weeks, depending on the severity of the case treated.

(c) An antiseborrheic lotion is prepared by mixing together the following ingredients:

| | |
|---|---|
| Compound of Example 5 | 0.030 g |
| Propylene glycol | 5.000 g |
| Butylhydroxytoluene | 0.100 g |
| Ethanol (at 95°) q.s. | 100.000 g |

This lotion will be applied twice a day to a eborrheic scalp and a significant improvement is observed within 2 to 6 weeks.

(d) A cosmetic composition to counter the harmful effects of sunlight is prepared by mixing together the following ingredients:

| | |
|---|---|
| Compound of Example 7 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preserving agents | 0.300 g |
| Propylene glycol | 2.000 g |

| | |
|---|---|
| Triethanolamine | 0.500 g |
| Fragrance | 0.400 g |
| Demineralized water q.s. | 100.000 g |

This composition will be applied daily, and it combats light-induced ageing.

(e) The following nonionic oil-in-water cream is prepared:

| | |
|---|---|
| Compound of Example 10 | 0.500 g |
| Vitamin D3 | 0.020 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water q.s. | 100.000 g |

This cream will be applied to psoriatic skin 1 to 2 times a day for 30 days.

(f) A topical gel is prepared by mixing together the following ingredients:

| | |
|---|---|
| Compound of Example 9 | 0.050 g |
| Ethanol | 43.000 g |
| α-Tocopherol | 0.050 g |
| Carboxyvinyl polymer sold under the name "Carbopol 941" by the company "Goodrich" | 0.500 g |
| Triethanolamine as an aqueous 20% by weight solution | 3.800 g |
| Water | 9.300 g |
| Propylene glycol q.s. | 100.000 g |

This gel will be applied in the treatment of acne 1 to 3 times a day for 6 to 12 weeks, depending on the severity of the case treated.

(g) A hair lotion to combat hair loss and to stimulate hair growth is prepared by mixing together the following ingredients:

| | |
|---|---|
| Compound of Example 1 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylhydroxyanisole | 0.01 g |
| Butylhydroxytoluene | 0.02 g |
| Water q.s. | 100.00 g |

This lotion will be applied twice a day for 3 months to a scalp which has suffered considerable hair loss.

(h) An anti-acne cream is prepared by mixing together the following ingredients:

| | |
|---|---|
| Compound of Example 3 | 0.050 g |
| Retinoic acid | 0.010 g |
| Mixture of glyceryl stearate and polyethylene glycol stearate (75 mol) | 15.000 g |
| sold under the name "Gelot 64" by the company "Gattefosse" | |
| Kernel oil polyoxyethylenated with 6 mol of ethylene oxide, sold under the name "Labrafil M2130 CS" by the company "Gattefosse" | 8.000 g |
| Perhydrosqualene | 10.000 g |
| Preserving agents | qs |
| Polyethylene glycol (molecular mass = 400) | 8.000 g |
| Disodium salt of ethylenediamine-tetraacetic acid | 0.050 g |
| Purified water q.s. | 100.000 g |

This cream will be applied to skin affected with dermatitis or to acneic skin 1 to 3 times a day for 6 to 12 weeks.

(i) An oil-in-water cream is prepared by producing the following formulation:

| | |
|---|---|
| Compound of Example 7 | 0.020 g |
| Betamethasone 17-valerate | 0.050 g |
| S-Carboxymethylcysteine | 3.000 g |
| Polyoxyethylene stearate (40 mol of ethylene oxide) sold under the name "Myrj 52" by the company "Atlas" | 4.000 g |
| Sorbitan monolaurate polyoxyethylenated with 20 mol of ethylene oxide, sold under the name "Tween 20" by the company "Atlas" | 1.800 g |
| Mixture of glyceryl mono- and distearate sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | q.s. |
| Perhydrosqualene | 18.000 g |
| Mixture of caprylic/capric triglycerides sold under the name "Miglyol 812" by the company "Dynamit Nobel" | 4.000 g |
| Triethanolamine (99% by weight) | 2.500 g |
| Water q.s. | 100.000 g |

This cream will be applied twice a day to skin affected with dermatitis, for 30 days.

(j) The following oil-in-water cream is prepared:

| | |
|---|---|
| Lactic acid | 5.000 g |
| Compound of Example 2 | 0.020 g |
| Polyoxyethylene stearate (40 mol of ethylene oxide) sold under the name "Myrj 52" by the company "Atlas" | 4.000 g |
| Sorbitan monolaurate, polyoxyethylenated with 20 mol of ethylene oxide, sold under the name "Tween 20" by the company "Atlas" | 1.800 g |
| Mixture of glyceryl mono- and distearate sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | q.s. |
| Perhydrosqualene | 18.000 g |

-continued

| | |
|---|---|
| Mixture of caprylic/capric triglycerides sold under the name "Miglyol 812" by the company "Dynamit Nobel" | 4.000 g |
| Water q.s. | 100.000 g |

This cream will be applied once a day and helps combat both light-induced and chronological ageing.

What is claimed is:

1. A biaromatic compound corresponding to formula (I):

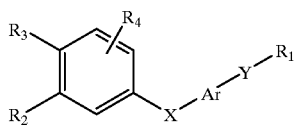

(I)

wherein $R_1$ is selected from:

(i) the radical —$CH_3$
(ii) the radical —$CH_2$—O—$R_5$
(iii) the radical —O—$R_5$, or
(iv) the radical —CO—$R_6$ wherein $R_5$ and $R_6$ have the meanings given below;

Y is selected from the radicals of formulae (a) to (c) below:

 (a)

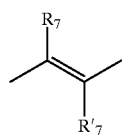 (b)

 (c)

wherein $R_7$, $R'_7$ and n have the meanings given below;

Ar is selected from the radicals of formulae (d) to (g) below:

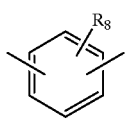 (d)

 (e)

 (f)

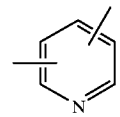 (g)

wherein $R_8$ has the meaning given below;

X is selected from the radicals of formulae (h), (j), (k), (l), (n), (o) or (p) below:

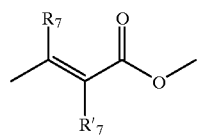 (h)

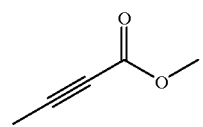 (j)

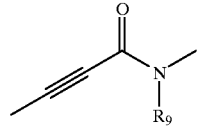 (k)

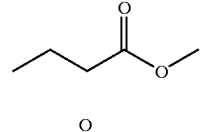 (l)

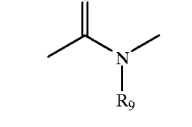 (n)

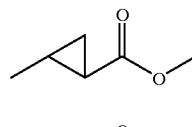 (o)

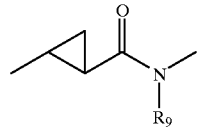 (p)

wherein, when X is the radical of formula (n), Y cannot be the radical of formula (a), and $R_7$, $R'_7$ and $R_9$ have the meanings given below;

$R_2$ and $R_3$, which may be identical or different, is an atom or a radical selected from:
(i) a hydrogen atom,
(ii) a linear or branched alkyl radical having from 1 to 20 carbon atoms,
(iii) a radical —$OR_5$, or
(iv) a radical —$SR_5$, wherein $R_5$ has the meaning given below, and at least one of $R_2$ and $R_3$ is a radical (ii);

wherein $R_2$ and $R_3$, taken together, can form, with the adjacent aromatic ring, a 5- or 6-membered ring optionally substituted with methyl groups and/or optionally interrupted by an oxygen or sulphur atom, $R_4$ and $R_8$, which may be identical or different, is a hydrogen atom, a halogen atom, a linear or branched alkyl radical having from 1 to 20 carbon atoms or a radical —$OR_5$;

$R_5$, which may be identical or different, is a hydrogen atom, a lower alkyl radical or a radical —$COR_{10}$, wherein $R_{10}$ has the meaning given below;

$R_6$ is an atom or a radical selected from:
 (a) a hydrogen atom,
 (b) a lower alkyl radical, or
 (c) a radical of formula:

wherein R' and R" have the meanings given below, or
 (d) a radical —$OR_{11}$,
 wherein $R_{11}$ has the meaning given below;

$R_7$, $R'_7$, and $R_9$, which may be identical or different, is a hydrogen atom or a lower alkyl radical;

n is equal to 0, 1 or 2;

$R_{10}$ is a lower alkyl radical;

$R_{11}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue;

R' and R", which may be identical or different, is a hydrogen atom, a lower alkyl radical, a mono- or polyhydroxyalkyl radical, an optionally substituted aryl radical or an amino acid or peptide or sugar residue, or alternatively, taken together, form a heterocycle; or the optical and geometrical isomers of the compounds of formula (I), or the salts thereof.

2. A compound according to claim 1, which is in the form of a salt of an alkali metal or alkaline-earth metal, of an organic amine, or of an inorganic or organic acid.

3. A compound according to claim 1, which is:
4-[3-(5,6,7,8-Tetrahydro-5,5,8,8-tetramethyl-2-naphthyl)acryloyloxy]benzoic acid;
4-[3-(5,6,7,8-Tetrahydro-5,5,8,8-tetramethyl-2-naphthyl)propanoyloxy]benzoic acid;
4-[3-(5,6,7,8-Tetrahydro-5,5,8,8-tetramethyl-2-naphthyl)-2-butenoyloxy]benzoic acid;
3-[3-(5,6,7,8-Tetrahydro-5,5,8,8-tetramethyl-2-naphthyl)acryloyloxy]benzoic acid;
4-(5,6,7,8-Tetrahydro-5,5,8,8-tetramethyl-2-naphthyloxycarbonylvinyl)benzoic acid;
4-[3-(5,6,7,8-Tetrahydro-5,5,8,8-tetramethyl-2-naphthyl)propynoyloxy]benzoic acid;
4-[3-(5,6,7,8-Tetrahydro-5,5,8,8-tetramethyl-2-naphthyl)acryloyloxy]benzaldehyde;
4-[3-(5,6,7,8-Tetrahydro-5,5,8,8-tetramethyl-2-naphthyl)acryloyloxy]benzenemethanol;
Allyl (E)-2-[3-(3,5,5,8,8,-pentamethyl-5,6,7,8-tetrahydro-2-naphthyl)acryloyloxy]benzoate;
(E)-2-[3-(3,5,5,8,8-Pentamethyl-5,6,7,8-tetrahydro-2-naphthyl)acryloyloxy]benzoic acid;
Allyl (E)-2-[3-(5,5,8,8-tetramethyl-5,6,7,8-tetrahydro-2-naphthyl)acryloyloxy]benzoate;
2-[3-(5,5,8,8-Tetramethyl-5,6,7,8-tetrahydro-2-naphthyl)acryloyloxy]benzoic acid;
2-[3-(5,5,8,8-Tetramethyl-5,6,7,8-tetrahydro-2-naphthyl)but-2-enoyloxy]benzoic acid;
4-[2-(5,5,8,8-Tetramethyl-5,6,7,8-tetrahydro-2-naphthyl)cyclopropanecarbonyloxy]benzoic acid; or
4-{[2-(5,5,8,8-Tetramethyl-5,6,7,8-tetrahydro-2-naphthyl)cyclopropanecarbonyl]amino}-benzoic acid, and mixtures thereof.

4. A method for preventing or treating dermatological complaints associated with a keratinization disorder which optionally has a bearing on differentiation and on proliferation; dermatological complaints associated with a keratinization disorder having an inflammatory and/or immunoallergic component; inflammatory complaints which do not exhibit a keratinization disorder; dermal or epidermal proliferations, whether benign or malignant and whether or not they are of viral origin; bullosis and collagen diseases; ophthalmological disorders; light-induced and/or chronological aging of the skin or actinic keratoses and pigmentations, or any pathology associated with chronological or actinic ageing; the stigmata of epidermal and/or dermal atrophy induced by local or systemic corticosteroids, or any other form of skin atrophy; cicatrization disorders or for preventing or repairing vibices; disorders of sebaceous functioning; cancerous or precancerous states; inflammatory conditions; any complaint of viral origin on the skin or generally; alopecia; dermatological complaints having an immunological component; complaints of the cardiovascular system; or skin disorders due to exposure to UV radiation or promoting cicatrization; said method comprising administering an effective amount of the compound according to claim 12 to prevent, treat or promote said condition to a human or animal in need of such prevention, treatment or promotion.

5. A pharmaceutical composition comprising, in a pharmaceutically acceptable support, an effective amount of at least one of the compounds according to claim 1.

6. A pharmaceutical composition according to claim 5, wherein the concentration of said compound(s) is between 0.001% and 5% by weight relative to the composition as a whole.

7. A cosmetic composition comprising, in a cosmetically acceptable support, an effective amount of at least one of the compounds according to claim 1.

8. A cosmetic composition according to claim 7, wherein the concentration of said compound(s) is between 0.001% and 3% by weight relative to the composition as a whole.

9. A cosmetic composition according to claim 7, comprising a cosmetically acceptable support for body or hair hygiene.

* * * * *